(12) United States Patent
Wilmot et al.

(10) Patent No.: US 7,708,719 B2
(45) Date of Patent: May 4, 2010

(54) MEDICAMENT CONTAINER, A MEDICAMENT DISPENSING KIT FOR ADMINISTERING MEDICATION AND A METHOD FOR PACKAGING THE SAME

(75) Inventors: John G. Wilmot, Mount Airy, MD (US); C. Michael Mesa, Boyds, MD (US)

(73) Assignee: Meridian Medical Technologies, Inc., Columbia, MD (US)

( * ) Notice: Subject to any disclaimer, the term of this patent is extended or adjusted under 35 U.S.C. 154(b) by 2134 days.

(21) Appl. No.: 10/285,692

(22) Filed: Nov. 1, 2002

(65) Prior Publication Data

US 2003/0106824 A1    Jun. 12, 2003

Related U.S. Application Data

(60) Provisional application No. 60/330,945, filed on Nov. 2, 2001, provisional application No. 60/350,972, filed on Jan. 25, 2002.

(51) Int. Cl.
| | |
|---|---|
| A61F 5/44 | (2006.01) |
| A61C 15/00 | (2006.01) |
| A61B 19/02 | (2006.01) |
| A61B 17/06 | (2006.01) |
| B65D 83/10 | (2006.01) |

(52) U.S. Cl. .............. 604/236; 604/232; 604/187; 206/364; 206/438

(58) Field of Classification Search ............ 604/96, 604/131, 82–92, 134, 135, 140, 181, 187, 604/200–207, 232–236; 206/364, 438
See application file for complete search history.

(56) References Cited

U.S. PATENT DOCUMENTS

| | | | | |
|---|---|---|---|---|
| 2,735,799 | A | * | 2/1956 | Abramson ............ 514/653 |
| 4,150,744 | A | | 4/1979 | Fennimore |
| 4,394,863 | A | * | 7/1983 | Bartner ............ 604/90 |
| 4,553,962 | A | | 11/1985 | Brunet |
| 4,869,398 | A | | 9/1989 | Colvin et al. |
| 4,872,553 | A | * | 10/1989 | Suzuki et al. ......... 206/524.4 |
| 5,334,162 | A | * | 8/1994 | Harris ............ 604/232 |
| 5,354,286 | A | | 10/1994 | Mesa et al. |
| 5,364,369 | A | | 11/1994 | Reynolds |
| 5,383,864 | A | | 1/1995 | Van Den Heuvel |
| 5,483,973 | A | | 1/1996 | Benson et al. |
| 5,531,683 | A | * | 7/1996 | Kriesel et al. .......... 604/89 |
| 5,569,236 | A | | 10/1996 | Kriesel |
| 5,586,975 | A | | 12/1996 | Tanaka et al. |
| 5,605,542 | A | | 2/1997 | Tanaka et al. |
| 5,620,423 | A | | 4/1997 | Eykmann et al. |
| 5,654,054 | A | | 8/1997 | Tropsha et al. |
| 5,716,339 | A | | 2/1998 | Tanaka et al. |
| 5,720,729 | A | * | 2/1998 | Kriesel ............ 604/132 |
| 5,723,189 | A | | 3/1998 | Sudo |
| 5,749,968 | A | | 5/1998 | Melanson et al. |
| 5,782,815 | A | | 7/1998 | Yanai et al. |

(Continued)

FOREIGN PATENT DOCUMENTS

EP    1 146 071 A2    10/2001

*Primary Examiner*—Matthew F Desanto
(74) *Attorney, Agent, or Firm*—Jones Day; Garry J. Tuma (57) ABSTRACT

A medicament container, medicament dispensing kit and packaging process that minimizes exposure of the medication to oxygen to prevent degradation of the medication are disclosed.

60 Claims, 5 Drawing Sheets

U.S. PATENT DOCUMENTS

| | | |
|---|---|---|
| 5,817,056 A | 10/1998 | Tanaka et al. |
| 5,833,653 A | 11/1998 | Vetter et al. |
| 5,855,907 A | 1/1999 | Peyman |
| 5,865,799 A | 2/1999 | Tanaka et al. |
| 5,939,425 A | 8/1999 | Caruso |
| 6,043,244 A | 3/2000 | Caruso |
| 6,210,369 B1 | 4/2001 | Wilmot et al. |
| 6,315,112 B1 * | 11/2001 | Garrill et al. ................. 206/204 |
| 6,620,135 B1 * | 9/2003 | Weston et al. ................ 604/140 |

* cited by examiner

FIG. 13

MEDICAMENT CONTAINER, A MEDICAMENT DISPENSING KIT FOR ADMINISTERING MEDICATION AND A METHOD FOR PACKAGING THE SAME

CROSS REFERENCE TO RELATED APPLICATIONS

This application claims priority from U.S. Provisional Application Ser. No. 60/330,945, filed Nov. 2, 2001 and U.S. Provisional Application Ser. No. 60/350,972, filed Jan. 25, 2002. These disclosures are incorporated herein in their entirety by reference.

FIELD OF THE INVENTION

The present invention relates to medicament dispensing mechanisms for administering a predetermined dosage of medication. In one embodiment, the present invention is directed to a medicament dispensing kit or injector used for dispensing a gas sensitive medication (e.g., dihydroergotamine (DHE) and epinephrine) that limits the exposure of the medication to the undesirable gas thereby improving and maintaining the effectiveness of the medication over time. The present invention is also directed to method of producing a kit that limits exposure of the medication to the undesirable gas (e.g., oxygen). The present invention is also directed to a method of storing a medicament in an autoinjector for prolonged periods, and then administering the medicament contained therein.

BACKGROUND OF THE INVENTION

Migraine headaches or migraines are generally described as recurrent severe headaches, which can be disabling to the sufferer. The duration of migraines can last up to seventy-two (72) hours and be accompanied nausea, vomiting and sensitivity to light. It is generally agreed that to successfully treat a migraine, concentrations of an anti-migraine drug in the bloodstream must reach a therapeutic level within a certain time from the onset of the migraine headache in order to be effective in reducing and/or eliminating the migraine headache. DHE is effective for the treatment of migraines. DHE can be administered intramuscularly, subcutaneously, as a nasal spray, or by other delivery routes.

DHE (as with other medicaments), however, degrades when exposed to oxygen. To be effective, the dissolved oxygen content needs to be maintained below at least 2 ppm and more preferably around 0.5 ppm. At present, DHE is only available in ampoules for injection using a manual syringe or for use in a nasal spray. The ampoules protect the medication from oxygen exposure while stored within the ampoule. The use of ampoules, however, requires the user to carryout a number of manipulations prior to use including breaking open the ampoule in order to either draw the medication into a syringe or inserting the opened ampoule into a nasal spray for use. Breaking the ampoule may be hazardous because it may produce shards of glass or particles that may mix with the medication and be injected or inhaled by the migraine sufferer. While the ampoule is open and prior to insertion in either the syringe or the nasal sprayer, the DHE is exposed to oxygen, which can lead to degradation of the DHE. Furthermore, DHE is often self administered by the migraine sufferer. Self administration occurs while the sufferer may be experiencing reduced functional and concentration abilities. As such, the sufferer may improperly administer the correct dosage of medication or take an over or under dosage of the medication.

There is a need for a safe and effective method of storing and administering medicaments, such as DHE, that protects against oxygen degradation and allows a migraine sufferer to self administer a predetermined dosage of medication.

OBJECTS OF THE INVENTION

It is therefore an object of the present invention to provide a packaging system for medication that minimizes exposure to oxygen while permitting easy self administering.

It is another object of the present invention to provide a packaging system for medication that limits degradation of the medication.

It is another object of the present invention provide a medicament dispensing kit that provides for the stable storage of a dose of an oxygen sensitive medicament (e.g., DHE or epinephrine).

It is another object of the present invention to provide a medicament dispensing kit that minimizes the exposure of a dose of DHE to oxygen.

It is another object of the present invention to provide a medicament dispensing assembly that does not require the use of an ampoule to store the medication.

It is another object of the present invention to provide a single use medicament dispensing kit that enables a user to self administer a dose of medication.

It is yet another object of the present invention to provide a packaging assembly that stores a single dose of medication in a protective environment.

It is yet another object of the present invention to provide a packaging system that extends the shelf life of the medicament.

It is another object of the present invention to provide secondary packaging to prevent puncturing or damage to the oxygen barrier.

Additional objects and advantages of the invention are set forth, in part, in the description which follows, and, in part, will be apparent to one of ordinary skill in the art from the description and/or practice of the invention.

SUMMARY OF THE INVENTION

In response to the foregoing challenges, applicants have developed an innovative medicament container, medicament dispensing kit and packaging process that minimizes exposure of the medication to oxygen to prevent degradation of the medication.

The present invention is directed to a medicament dispensing kit for administering a predetermined dose of medication. It is contemplated that the medicament dispensing kit may be used by an individual for self medication and/or treatment. It is further contemplated that the medicament dispensing kit may be used by a health care professional to administer a predetermined dose of medication for a patient. In accordance with the present invention, each medicament dispensing kit includes a predetermined dose of medication. The predetermined dose of medication may include DHE. The invention, however, is not limited to the use of DHE; rather, other oxygen sensitive medications including epinephrine or medications that degrade with prolonged exposure to oxygen or other undesirable gases are contemplated for use and are considered to be within the realm of the present invention. It is also contemplated to use the present invention in connection with the storage of medications for the purpose of increasing shelf life. As such, it is contemplated that the present invention may be used in connection with any medicament that is stored for prolonged periods of time.

In accordance with the present invention, the predetermined dose of medication is stored in a medicament container, which was filled in an inert gas environment, which may be provided in an isolator, a tunnel, through a flush of inert gas or a shower of inert gas. The medicament container includes a cartridge assembly, which receives the predetermined dose of medication. The cartridge assembly may be formed from glass or another suitable material. The cartridge assembly has at least one opening formed therein to facilitate filling and dispensing of the dose of medication. Each opening contains at least one sealing assembly. It is contemplated that the sealing assemblies may be formed from a rubber or other material that functions as an oxygen absorbing material or an oxygen barrier material. It is also contemplated that one sealing assembly may be formed from an absorbing material and another sealing assembly may be formed from a barrier material. It is further contemplated that one or more of the sealing assemblies may be formed from an oxygen permeable material, whereby the oxygen absorbing material may withdraw oxygen from the system through the seal. One of the sealing assemblies is movable within the interior portion of the cartridge assembly in response to activation of a dispensing assembly to facilitate the dispensing of the dose of medication. This sealing assembly is positioned within the interior portion of the container prior to filling with the dose of medication.

Another sealing assembly is located in another opening in the cartridge assembly after the cartridge assembly is filled with the dose of medication. This sealing assembly may include a venting assembly for venting the inert gas from an interior of the cartridge assembly after the predetermined dose of medication has been located therein. The inert gas is removed under vacuum pressure. It is also contemplated that it is not necessary to remove all of the inert gas within the cartridge assembly. A partial vacuum may be used to remove a portion of the gas. The sealing assembly moves from a sealing position to a dispensing position in response to activation of the dispensing assembly. Alternatively, the sealing assembly may be placed over the neck portion of the cartridge assembly. The sealing assembly is punctured in response to actuation of the dispensing assembly and more particularly movement of a needle assembly. The sealing assembly is punctured by the needle assembly. Alternatively, it is contemplated to provided a diaphragm sealing assembly, wherein the diaphragm is ruptured in response to increased pressure by the medicament in response to activation of the dispensing assembly.

In accordance with the present invention, the medicament container may further include a dispensing element for administering the predetermined dose of medication from the medicament container in response to activation of the dispensing assembly. In the case of an auto-injector or a syringe, the dispensing element may be a needle for injecting the predetermined dose of medication into the user upon activation of the dispensing assembly.

The kit accordance with the present invention further includes a dispensing assembly adapted to receive the medicament container therein. The dispensing assembly dispenses the predetermined dose of medication upon activation by a user. The dispensing assembly may be an auto-injector, a syringe, a nasal sprayer, a needle free auto-injector or other drug delivery system. The dispensing assembly is stored in a sealed package. The sealed package forms on oxygen barrier to prevent oxygen from penetrating the dispensing assembly to degrade the dose of medication. In accordance with the present invention, wherein the sealed package is a high barrier pouch, which prevents oxygen from entering the interior of the package. Preferably, the high barrier pouch is a laminated pouch having several layers. Furthermore, one of the layers is preferably a layer of an aluminum foil. It is contemplated that the high barrier pouch may be located within a rigid secondary packaging such as a rigid container or tube to prevent puncture of the barrier pouch. It is also contemplated that the sealed package may be formed as a rigid container or can formed from an oxygen barrier material such as aluminum or a suitable polymer. It is also contemplated that the sealed package may be a thermoformed package or a metal tube.

An inert gas is flushed through in the interior compartment of the sealed package when the dispensing assembly is placed in the package to remove the presence of any oxygen or undesired gas within the compartment. A gas absorbing material may be located in the sealed package to absorb any oxygen that may be out gassed from the dispensing assembly. It is contemplated that ascorbic acid, iron powder, borohydride or mordenite/calcium oxide systems or halon gas or equivalent materials may be used as a gas absorbing material. It is also contemplated that an gas absorbing material be omitted from the package. It is also contemplated that the interior compartment of the sealed package may be filled with an inert gas or air. It is further contemplated that the interior compartment may be sealed under vacuum to create a vacuum within the sealed package. This will limit the amount of air or gas within the sealed package at the onset. It is contemplated that a certain amount of air will permeate the seal of the package and be absorbed by the absorbing material. The presence of the vacuum will increase the useful life of the gas absorbing material by limiting the exposure of the material to the undesired gas at the onset.

The present invention is not limited to a single sealed package; rather, it is contemplated that the sealed package may include a plurality of separate sealed interior compartments. Each sealed compartment contains a dispensing assembly having the predetermined dose of medication located therein.

The present invention is also directed to a method of packaging a predetermined dose of medication. The packaging method reduces exposure of the medication to oxygen, which reduces degradation of the medication. The method includes providing a predetermined dose of medication, which is placed in a medicament container. The filling of the medicament container occurs in an environment containing an inert gas. The use of the inert gas (e.g., argon, nitrogen, $CO_2$ or halon) limits oxygen exposure. During the filling operation, the interior compartment of the medicament container is purged using the inert gas to eliminate the presence of oxygen.

The medicament container is then sealed in the inert gas environment, which may be provided by an isolator, a tunnel, through a flush of inert gas or a shower of inert gas. During the sealing operation, a sealing assembly is placed in an opening in the medicament container. The sealing assembly is located within the opening such that it is in a venting position to permit the removal of any remaining gas from medicament container. It is also contemplated that a portion of the inert gas may remain within the medicament container. A partial vacuum may be created within the container using the inert gas. The inert gas is then withdrawn from the medicament container by applying a vacuum to the medicament container. It is also contemplated that all of the inert gas, a portion of the inert gas or none of the inert gas is removed from the medicament container. The sealing is then seated in the opening to a sealing position while the medicament container is still subject to the vacuum. Alternatively, the sealing assembly may be placed around the neck portion of the cartridge assembly after the inert gas purge. The sealing assembly may include a portion that fits within the neck portion and a portion that extends around the neck portion of the cartridge assembly.

The medicament container is then placed in a dispensing assembly. The medicament container is positioned in the dispensing assembly such that the user can simply activate the dispensing assembly to dispense the predetermined dosage of the medication. As discussed above, it is contemplated that dispensing assembly may be a syringe, an auto-injector, a nasal sprayer or other suitable means for dispensing the predetermined dosage.

The loaded dispensing assembly is then located in a package. Prior to and during the locating of the dispensing assembly in the package, the interior of the package may be flushed with an inert gas to remove any oxygen. An oxygen absorbing material is located within the package. The oxygen absorbing material may be formed on the wall of the package, inserted as a separate packet within the package, or provided as a powder within the interior of the package, formed as part of one of the components of the drug delivery system (e.g. a component of the autoinjector), located in a compartment within the drug delivery system, or a separate component of the drug delivery system. The package may be filled with an inert gas to prevent shrinkage of the pouch created by the absence of air within the pouch. As discussed above, the package is designed to limit exposure of the medication to oxygen. Furthermore, the packaging and the packaging process are designed to limit oxygen exposure and absorb any oxygen that may be out gassed from the dispensing assembly once located in the package.

BRIEF DESCRIPTION OF THE DRAWINGS

The invention will be described in conjunction with the following drawing in which like reference numerals designate like elements and wherein.

DETAILED DESCRIPTION OF THE INVENTION

Figure 1:
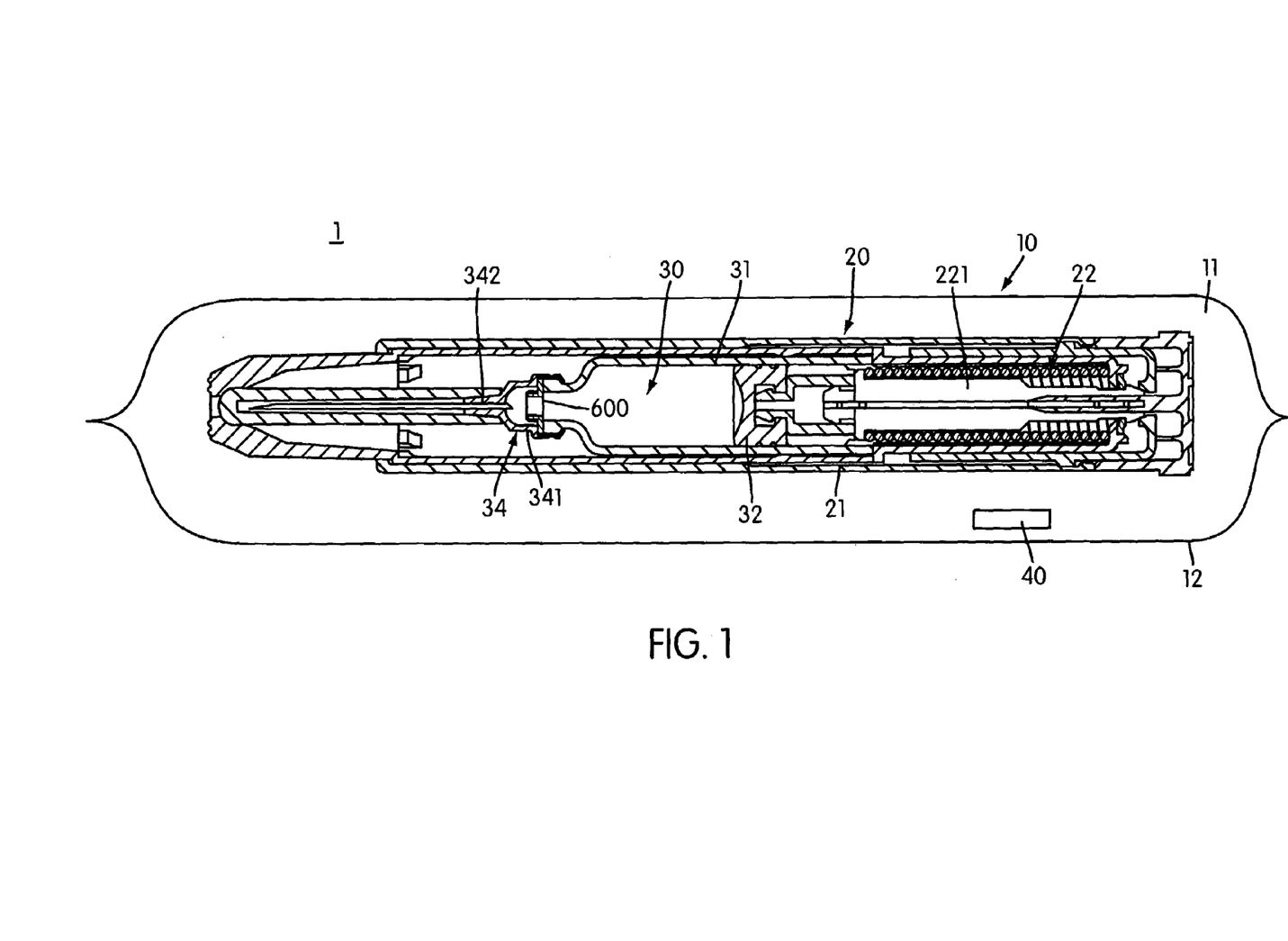
FIG. 1 is a cross sectional schematic view of a medicament dispensing kit in accordance with an embodiment of the present invention.

A medicament dispensing kit 1 is illustrated in FIG. 1. The kit 1 includes a sealed package 10, a medication dispensing assembly 20, and a medicament container 30. The kit 1 also includes an oxygen absorbing component 40.

Figure 3:
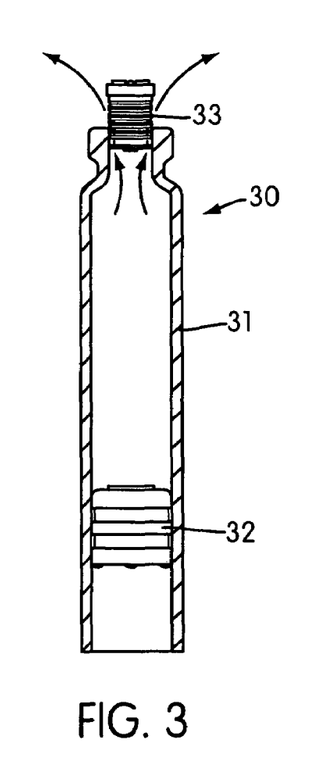
FIG. 3 is a cross sectional schematic view illustrating the location of the sealing assemblies and the container assembly during the venting operation whereby the inert gas is vented from the interior of the container assembly.
Figure 4:
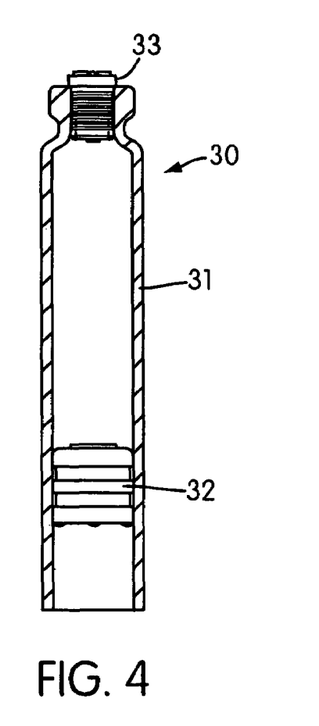
FIG. 4 is a cross sectional schematic view illustrating the location of the sealing assemblies and the container assembly in the sealed position after the venting operation.

The medicament container 30 will now be described in greater detail in connection with FIGS. 2-8. The medicament container 30 includes a cartridge assembly or vial 31 having an interior compartment for receiving a predetermined dose of medication. The cartridge assembly or vial 31 is preferably formed from glass. The present invention, however, is not limited to a cartridge assembly 31 formed from glass; rather, other materials that are non reactive with DHE or other oxygen sensitive medicaments and prevent the passage of oxygen there through are considered to be well within the scope of the present invention. The medicament container 30 also includes a pair of sealing assemblies 32 and 33 for sealing the open end portions of the cartridge assembly 31 as shown in FIG. 4. The sealing assemblies 32 and 33 are preferably formed from rubber. It is contemplated that the sealing assemblies 32 and 33 may be formed from a material (e.g., rubber or other suitable material) that has oxygen barrier capabilities (e.g., West 4405/50 or 4416/50 bromobutyl rubber) or oxygen absorbing capabilities (e.g., Diakyo 777 series rubber or PTFE). It is further contemplated that either of the sealing assemblies 32 and 33 may be formed from an oxygen permeable material to permit the passage of oxygen from the interior of the medicament container 30 to the oxygen or gas absorbing material. It is also contemplated that the medicament container 30 may be formed from an oxygen or gas permeable material to permit the withdrawal of oxygen or other undesirable gas from the interior of the medicament container 30 by the oxygen/gas absorbing material.

Figure 2:
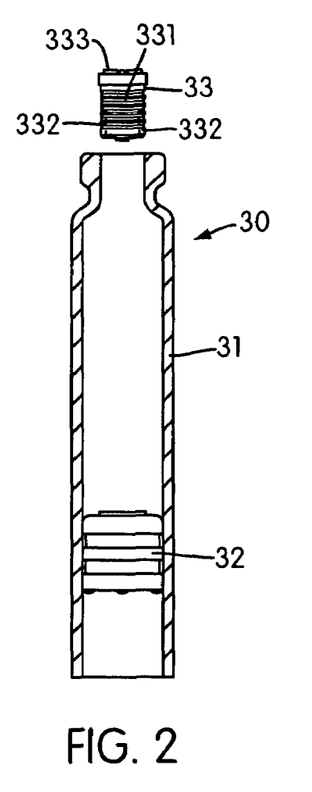
FIG. 2 is a cross sectional schematic view illustrating the sealing assemblies and the container assembly for the medicament container.
Figure 6:
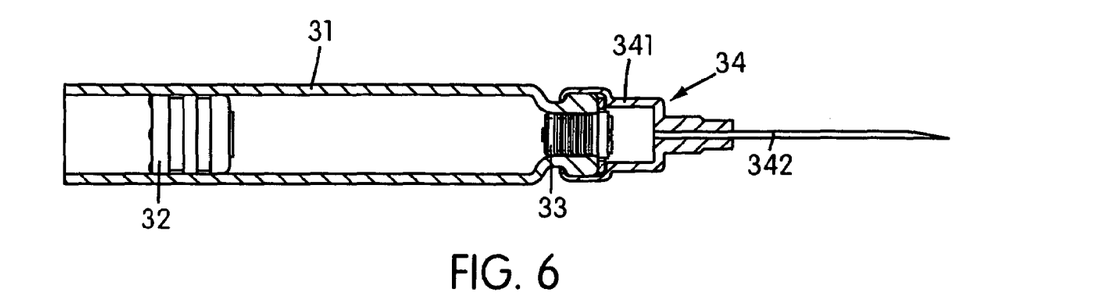
FIG. 6 is a cross sectional view of the medicament container illustrating the position of the sealing assembly in a storage position when the dispenser assembly is located in the sealed package.
Figure 7:
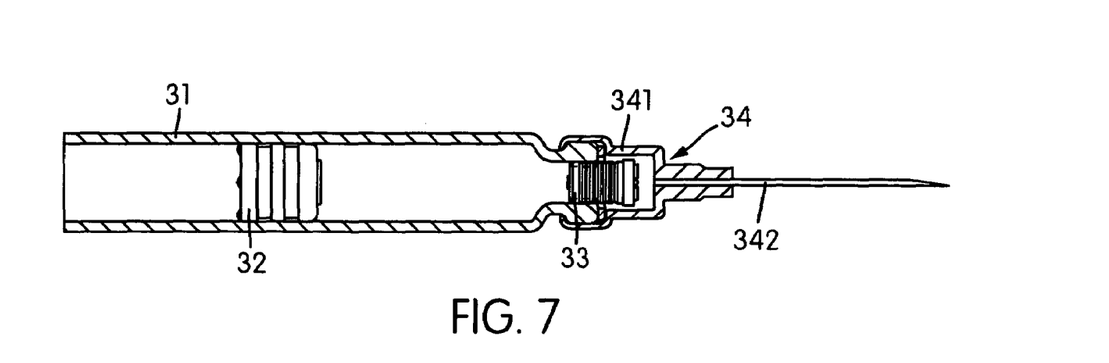
FIG. 7 is a cross sectional view of the medicament container illustrating the position of the sealing assembly upon activation of the dispenser assembly by the user.
Figure 8:
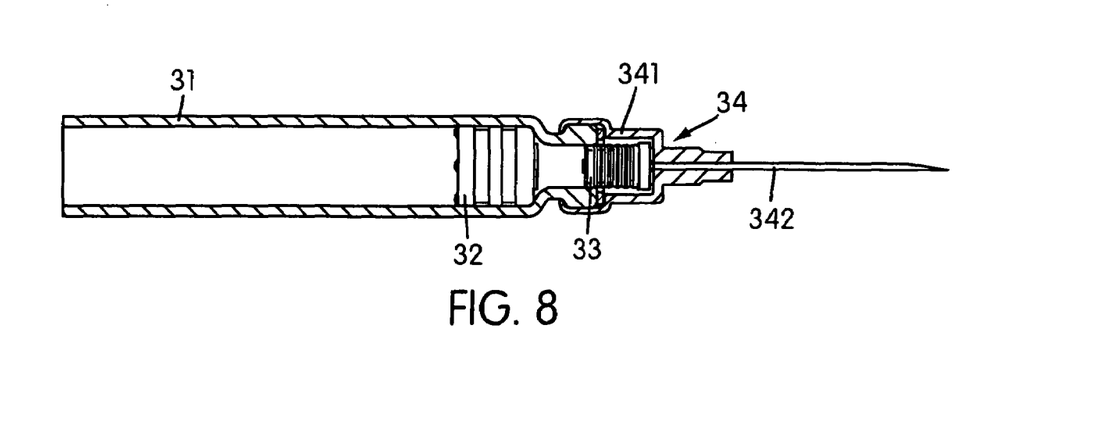
FIG. 8 is a cross sectional view of the medicament container illustrating the position of the sealing assembly in an ejection position whereby the medication is administered to the patient.

A first sealing assembly 32 is positioned in the interior compartment of the cartridge assembly 31, as shown in FIG. 2. The first sealing assembly 32 is adapted to frictionally engage the inner surface of the cartridge assembly 31 to prevent the medication from passing between the first sealing assembly 32 and the inner surface of the cartridge assembly 31. The first sealing assembly 32 is adapted to be engaged by an actuator element of the dispensing assembly 20, as shown in FIG. 1. Under the action of the dispensing assembly 20, the first sealing assembly 32 slides within the interior compartment of the cartridge assembly 31 towards the second sealing component 33, as shown in FIGS. 6-8. The movement of the first sealing assembly 32 pressurizes the medication within the cartridge assembly 31 to dislodge the second sealing component 33 to permit the administering of the medication. The medication may be administered through a dispensing element 34, as shown in FIGS. 1 and 6-8. The dispensing element 34 includes a housing 341 that is adapted to engage a neck portion 311 of the cartridge assembly 31. The dispensing element 34 also includes a needle assembly 342 for injecting the medication directly into the bloodstream, skin tissue or muscle tissue. The needle assembly 342 may be used when the dispensing assembly 20 is an auto-injector, a syringe, or an alternative drug delivery system. The present invention, however, is not limited to the use of a needle assembly 342; rather, the aspirating element may be provided to permit aspiration of the medication such that it can be dispensed through a nasal sprayer, needle free auto-injector, or alternative drug delivery system.

Figure 5:
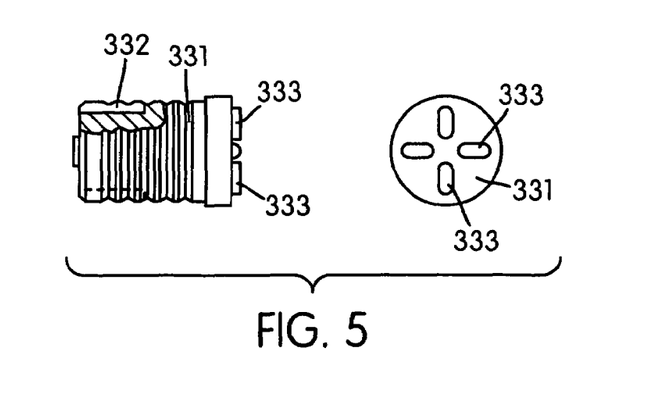
FIG. 5 is a cross sectional view of the sealing assembly for the medicament container in accordance with the present invention.

The second sealing component 33 is illustrated in greater detail in FIG. 5. Like the first sealing assembly 32, the second sealing component 33 includes a body portion 331 that is designed to frictionally engage the inner surface of the cartridge assembly 31 adjacent the neck portion 311. The second sealing component 32 further includes one or more venting passageways 332 formed in a portion of the exterior surface of the body portion 331. As described in greater detail below, the venting passageways 332 permit the venting of gases from the interior compartment of cartridge assembly 31 during the filling operation, as shown in FIG. 3. The venting passageways 332 further permit the passage of medication there through during the medication dispensing operation, as shown in FIG. 8. The body portion 331 of the second sealing component 33 includes a plurality of ribs or projections 333 extending from an end portion, as shown in FIG. 5. The ribs 333 are radially spaced around the perimeter of the second sealing component 33. During the dispensing operation, the second sealing component 33 moves from the position illustrated in FIG. 6 to the position illustrated in FIG. 8 whereby the ribs 333 of the second sealing component 33 contact an interior surface of the housing 341. The venting passageways 332 permit the passage of medication into the housing 341. The medication then travels through the space between the ribs 333 and interior surface of the housing 341 to the needle assembly 342. The space between the ribs 333 and interior surface of the housing 341 ensures a liquid communication path between the cartridge assembly 31 and the needle assembly. This space may also control the size of medication particles traveling through the needle assembly 342 to prevent clogging of the needle assembly 342.

The medicament container 30 is adapted to be received within a dispensing assembly 20. In accordance with one embodiment of the present invention, the dispensing assembly 20 is an auto-injector, as shown in FIG. 1. It is contemplated that the medicament container 30 may be used in a wide variety of single use auto-injectors as disclosed, for example but not limited to, in U.S. Pat. No. 4,031,893 to Kaplan et al., U.S. Pat. No. 5,295,965 to Wilmot et al., U.S. Pat. No. 5,102,393 to Sarnoff et al., and U.S. Pat. No. 5,092,843 to Monroe et al. The disclosures of each of these patents are specifically incorporated herein by reference. It is also contemplated that the medicament container 30 may be used in a multi-use auto-injector as disclosed, for example in, U.S. Pat. No. 5,085,642 to Sarnoff et al. The disclosure of this patent is specifically incorporated herein by reference. The present invention, however, is not limited to an auto-injector; rather other dispensing assemblies including but not limited to prefilled syringes, nasal sprayers, needle free auto-injectors and other medication administering devices are considered to be well within the scope of the present invention.

The auto-injector 20 illustrated in FIG. 1 includes a housing 21. The medicament container 30 is located within the housing 21. The auto-injector 20 further includes an operating assembly 22 located within the housing 21. The operating assembly 22 includes an actuator arm 221, which is adapted to engage the first sealing assembly 32. Upon actuation of the operating assembly 22, the biased actuator arm 221 moves the first sealing assembly 32 from the storage position illustrated in FIG. 6 through the dispensing position illustrated in FIG. 7 to the position illustrated in FIG. 8. The pressure within the interior compartment of the cartridge assembly 31 causes the second sealing component 33 to move to an extended position, as shown in FIG. 8, such that the dose of medication can be dispensed through the dispensing element 34.

The dispensing assembly 20 and the medicament container 30 are packaged in a sealed package 10. The sealed barrier package 10 prevents oxygen from entering the interior of the package 11 through the package walls 12. The package walls 12 are preferably formed as a laminate containing more than one layer. For example, each wall 12 of the package 10 preferably includes a layer of aluminum foil. The wall 12 may be formed with three laminate layers including polyethylene terephthalate (PET), aluminum foil and polyethylene (PE). Alternatively, the wall 12 may be formed with five laminate layers including biaxial nylon, polyvinyl dichloride (PVDC), low density polyethylene (LDPE), aluminum foil, another layer of LDPE and linear, low density polyethylene (LLDPE). The present invention is not limited to the above-described laminated layers. Various combinations of these materials are possible and are contemplated to be within the scope of the present invention provided these combinations provide a barrier to oxygen penetration. The laminated walls 12 form a package 10 having an interior compartment 11. The above-described dispensing assembly 20 containing the medicament container 30 are located within the compartment 11 prior to sealing the package 10. The package 10 can be sealed by any suitable means that would prevent the passage of oxygen into the interior compartment 11. To protect the package 10 from inadvertent rupture, the package 10 may be located in a rigid secondary package 90. It is also contemplated that the package 10 may be formed as a rigid container (such as for example a can) using aluminum or other suitable oxygen barrier materials. It is further contemplated that the package 10 may be thermoformed or formed as a rigid tube.

Figure 10:
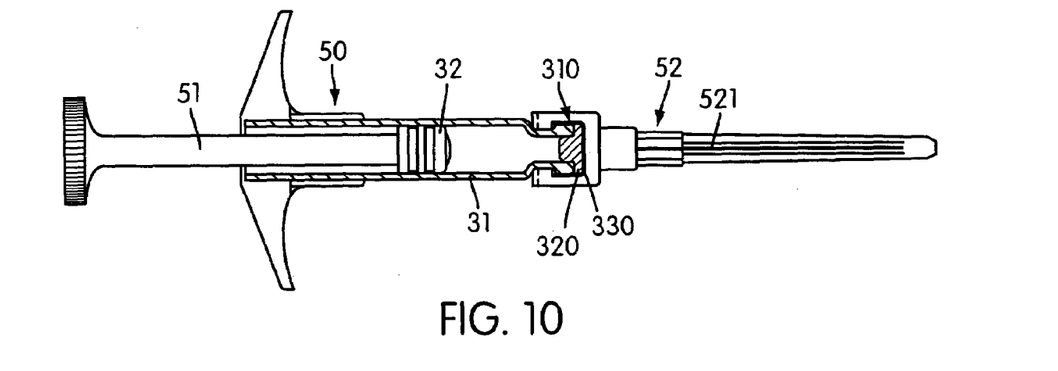
FIG. 10 is a cross sectional view of the medicament container of FIG. 9 located within a syringe.

To absorb any oxygen that may be present in the interior compartment 11, that may infiltrate the package 10 at the seal between, for example, the laminate layers or that may be out gassed from the dispensing assembly 20, an oxygen absorbing material 40 is located within the interior compartment. Ascorbic acid, iron powder, borohydride or mordenite/calcium oxide systems, or halon gas are all suitable oxygen absorbing materials. The oxygen absorbing material may be applied to the interior wall of the walls 12. A package 40 of the material may be located within the package 10, as shown in FIG. 10. Alternatively, the material may be placed in powder form within the compartment 11. The oxygen absorbing material may take the form of a self adhesive patch or disc 80 sewed to an inner wall of the package 10. It is also contemplated that one or more of the components of the dispensing assembly 20 may be formed from the oxygen absorbing material. It is also contemplated, but not preferred, that the interior compartment 11 may be evacuated of all gas so that a gas absorbing component is unnecessary.

Packaging the dispensing assembly 20 into a high barrier laminate package 10 preferable incorporating aluminum foil with an oxygen absorber and preferably an inert gas flush will provide a very good oxygen barrier to prevent ingress of oxygen into the pouch. The oxygen absorber will absorb any oxygen that maybe present in the pouch, in the dispensing assembly 20 and the medicament container 30, dissolved oxygen that may out gas from the assembly 20 and the container 30 and in particular the sealing assemblies 32 and 33. The absorber 40 will act as an oxygen sink to draw any extraneous oxygen out of the container 30. It is contemplated that a sufficient amount of the oxygen absorber will be provided to absorb any oxygen that permeates in through the seals in the package 10 over the expected lifetime of the product.

Figure 9:
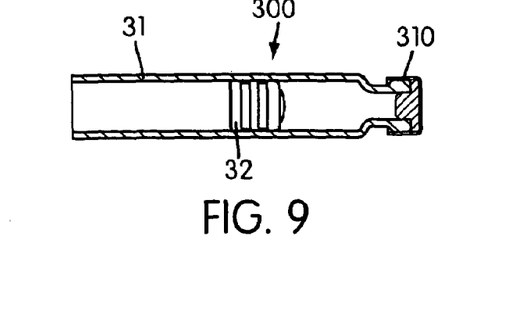
FIG. 9 is a cross sectional view of the medicament container in accordance with another embodiment of the present invention.
Figure 11:
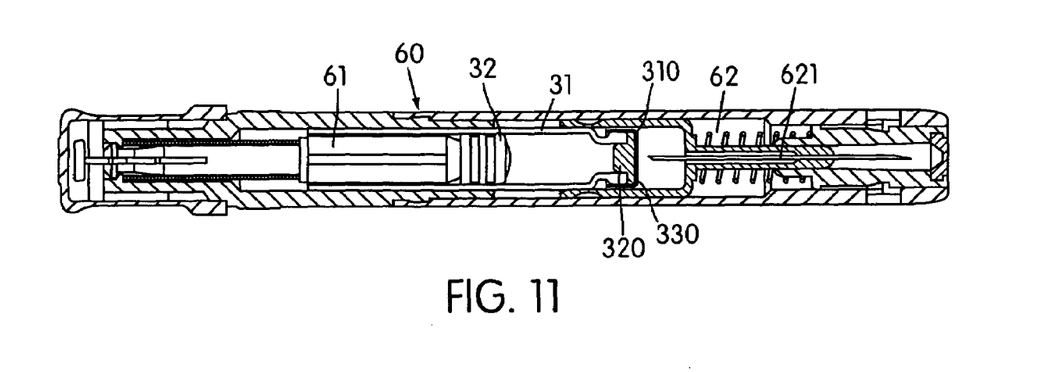
FIG. 11 is a cross sectional view of the medicament container of FIG. 9 located in an auto-injector.
Figure 12:
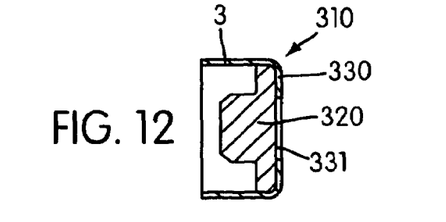
FIG. 12 is a cross sectional view of the sealing assembly of FIG. 9.

A variation of the medicament container 30 will be described in connection with FIG. 9. The medicament container 300 includes a cartridge assembly 31, as discussed above. A first sealing assembly 32 is located within the interior of the cartridge assembly 31. The sealing assembly 31 is adapted to engaged by the actuator assembly 51 of a syringe 50, as shown in FIG. 10, or the actuator assembly 61 of the auto-injector 60, as shown in FIG. 11. The medicament container 300 does not include a second assembly 33 that is received in an opening of the cartridge assembly 31. Instead, a sealing assembly 310 is provided. The sealing assembly 310 includes an inner sealing member 320, which is formed from a rubber material, as described above. As shown in FIG. 12, the sealing assembly 310 further includes an outer sealing member 330 formed as a metal cap assembly. The outer sealing member has a hole formed therein to permit the passage of the needle assembly 521 or 621 therethrough. A foil layer 331 may be provided to cover the hole prior to passage of the needle assembly 521 or 621 therethrough to prevent the passage of oxygen into the inner compartment 11. It is contemplated that the foil layer 331 may be positioned on the outer surface of the outer sealing member 330 or between the outer sealing member 330 and the inner sealing member 320. The outer sealing member is adapted to be crimped, screw fit or compression fit onto the neck portion of the cartridge assembly 31. The outer sealing member 330 provides an axial seal. The inner sealing member 320 provides an inner radial seal in the opening in the neck portion of the cartridge assembly 31. The second sealing assembly 310 is adapted to engage the outer surface and the inner surface of the neck portion of the cartridge assembly 31, as shown in FIG. 9. The outer sealing member 330 may be formed as a foil sheet that is laminated onto the top surface of the inner sealing member 320. The foil may be pierceable by the needle or an end of the actuator assembly. The foil is not intended to contact the medication. It is also contemplated that a reducing die could be used to push the sealing assembly into the cartridge assembly 31 without the use of vacuum pressure. It is also contemplated that a foil layer may be provided on the surface of the plunger 32.

Figure 13:
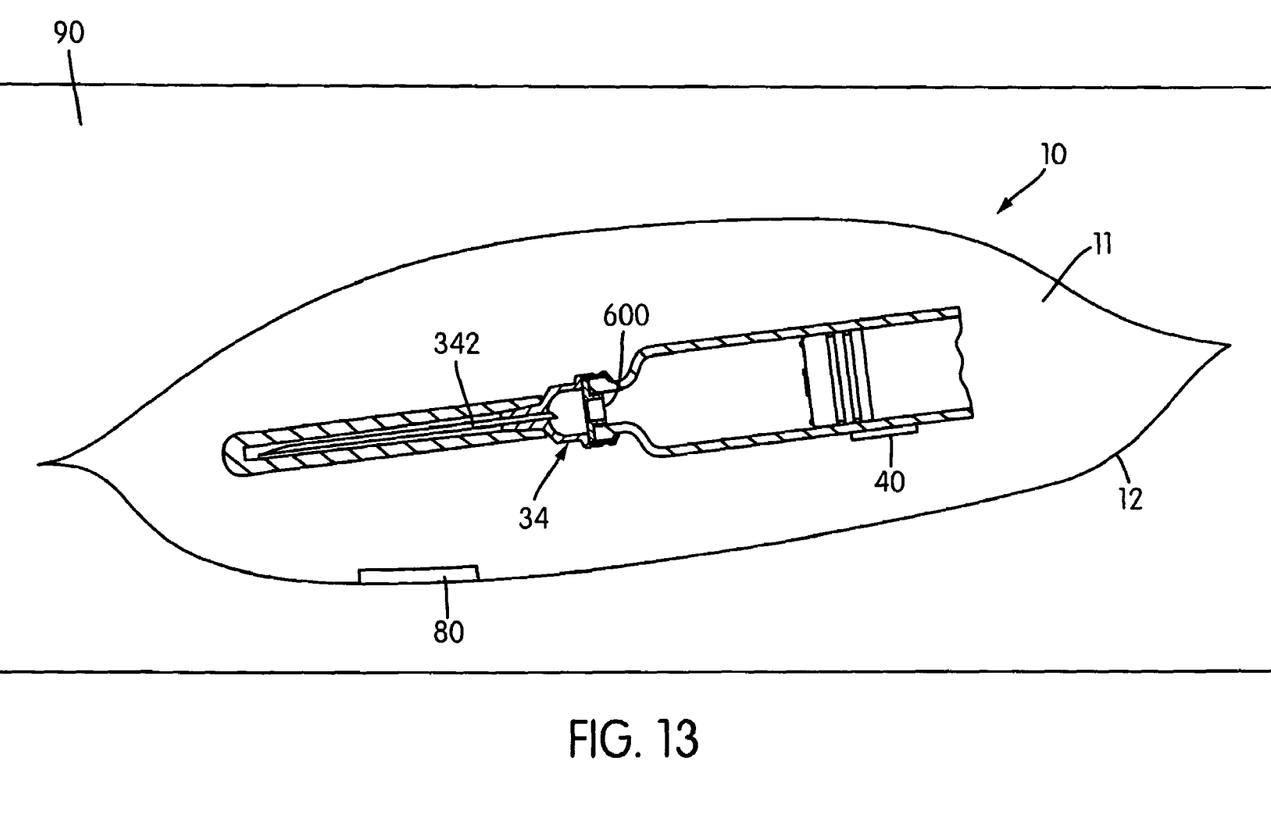
FIG. 13 is a cross sectional view of a medicament dispensing kit having a cartrix type dispensing assembly in accordance with an embodiment of the present invention.

A dispensing element 52 is adapted to engage the outer surface of the cartridge assembly 31 such that the sealing assembly 310 is sandwiched there between, as shown in FIG. 10. During operation, the actuator assembly 51 moves the first sealing assembly 32 within the interior compartment of the cartridge assembly 31. The pressure supplied by the user causes the needle assembly 521 to move towards the sealing assembly 310. In response, the sealing assembly 310 contacts an end portion of a needle assembly 521 in the dispensing element 52, which causes the needle assembly 521 to penetrate the inner sealing member 320. The dose of medication then passes through the needle assembly 521. For a syringe type dispensing element, the needle assembly 521 punctures the seal before the actuator assembly 51 is depressed. For a cartrix type dispensing assembly illustrated in FIG. 13, the diaphragm 600 expands and is ruptured after the actuator assembly has been actuated.

It is also contemplated that the present invention may be used in connection with a Hypak® syringe. With this arrangement, the needle assembly 342 is bonded or attached directly to the end of the cartridge assembly. The needle assembly 342 is located within a hole within the cartridge assembly, which preferably formed from glass. As such, the housing 341 can be eliminated. Furthermore, only one sealing assembly in contact with the medicament is necessary. An additional seal may be provided around the outer periphery of the needle assembly.

A dispensing element 62 is adapted to engage the outer surface of the cartridge assembly 31 such that the sealing assembly 310 is sandwiched there between, as shown in FIG. 11. During operation, the actuator assembly 61 moves the first sealing assembly 32 within the interior compartment of the cartridge assembly 31. In response, the cartridge assembly 31 and the sealing assembly 310 move within the dispensing assembly 60 in the direction of the needle assembly 621 in the dispensing element 62. After injection of the needle assembly 621 into the user, the end portion of the needle assembly 621 located within the dispensing assembly 60 penetrates the sealing assembly 310 such that the medication is then transmitted through the needle assembly 621 into the user. The operation of the needle assembly 621 penetrating a sealing assembly 310 is described in greater detail in U.S. Pat. No. 6,210,369 to Wilmot et al., the disclosure of which is hereby specifically incorporated herein by reference. The dose of medication then passes through the needle assembly 621. It is preferably that the inner sealing assembly 320 extend into the neck portion of the cartridge assembly 31 to provide a radial seal and increased protection against oxygen penetration. It, however, is contemplated that the size the inner sealing member 320 that projects into the opening of the neck portion may be reduced or eliminated, as shown for example in FIG. 9. This, however, may result in increased oxygen penetration.

The packaging process will now be described. The packaging method reduces exposure of the medication to oxygen. Thus, reducing degradation of the medication. The method includes providing a predetermined dose of medication, which is placed in a medicament container 30. The filling of the medicament container 30 occurs in an environment containing an inert gas. The inert gas may be located in an isolator, a tube or tunnel containing a flush of inert gas or a shower of inert gas. The use of the inert gas (e.g., argon or nitrogen), which is heavier than oxygen, reduces oxygen exposure. During the filling operation, the interior compartment of the cartridge assembly 31 is purged using the inert gas to eliminate the presence of oxygen. It is also contemplated that the cartridge assembly 31 may be filled from either open end.

The cartridge assembly 31 is then sealed in the inert gas environment. During the sealing operation, the sealing assembly 33 is placed in an opening in the cartridge assembly 31, as shown in FIG. 3. The sealing assembly 33 is located within the opening such that it is in a venting position to permit the removal of any remaining gas from the interior compartment of the cartridge assembly 31. The inert gas is then withdrawn from the cartridge assembly 31 by applying a vacuum. It is not necessary to remove all of the inert gas. The sealing assembly 33 is then seated in the opening to a sealing position by the application of pressure to the sealing assembly 33 while the medicament container 30 is still subject to the vacuum. It is also contemplated that a reducing die could be used to push the sealing assembly into the cartridge assembly 31 without the use of vacuum pressure. The venting operation is not performed when the sealing assembly 310 is used.

The medicament container 30 is then placed in a dispensing assembly 20. The medicament container 30 is positioned in the dispensing assembly 20 such that the user can simply activate the operating assembly 22 of dispensing assembly 20, as shown for example in FIG. 1, to dispense the predetermined dosage of the medication. As discussed above, it is contemplated that dispensing assembly 20 may be a syringe, as shown in FIG. 10, an auto-injector, as shown in FIGS. 1 and 11, a nasal sprayer or other suitable means for dispensing the predetermined dosage. It is also contemplated that the dispensing assembly 20 may be more tightly sealed to prevent the passage of oxygen or gas if the gas absorbing material is located within the assembly 20.

In one embodiment, the gas absorbing material 40 is a separate member that is stored within a space within the autoinjector housing 21, and in gaseous communication with the medicament cartridge assembly. In such embodiment, it may be desirable (though not required) to manufacture components of the dispensing assembly 20 itself substantially impervious to air to shield the gas absorbing material 40 from air. In this embodiment, the outer package 12 can be dispensed with.

The loaded dispensing assembly 20 is then located in a package 10. Prior to and during the locating of the dispensing assembly 20 in the package 10, the interior of the package 10 is flushed with an inert gas to remove any oxygen. It is not necessary to perform this operation, but it is preferable because it reduces the stress on the oxygen absorbing material thereby permitting the material to withdraw more oxygen from the components. An oxygen absorbing material 40 is located within the package 10. The oxygen absorbing material 40 may be formed on the wall of the package, inserted as a separate packet, as shown in FIG. 1 within the package or powder within the interior of the package or as part of the dispensing assembly 20. As discussed above, the package 10 is designed to limit exposure of the medication to oxygen. Furthermore, the packaging 10 and the packaging process are designed to limit oxygen exposure and absorb any oxygen that may be out gassed from the dispensing assembly 20 once located in the package 10. The containers 11 are filled in an argon or inert gas environment, may be inspected and packaged in air as quickly as possible to minimize the exposure of the medicament to oxygen or other undesired gases. The inert gas environment may be provided by means of an isolator, a tunnel, through a flush of inert gas or a shower of inert gas The above described medicament container, kit and packaging process simplify the use of DHE and other oxygen sensitive medications, while improving the stability of DHE. Furthermore, the dispensing assembly 20 provides for standard easier use allowing immediate easy use by the patient without significant manipulation or assembly. The dispensing assembly 20 will be user friendly, more convenient & provide better dosing accuracy over an ampoule based system. This is particularly important for the migraine application during patient self-injection when patient's functional and concentration abilities are reduced, their vision maybe impaired & they maybe feeling nausea. It will be apparent to those skilled in the art that various modifications and variations may be made without departing from the scope of the present invention. Although the present invention has been described in connection with the treatment of migraines using DHE, it is contemplated that various medications including epinephrine may be employed while practicing the present invention. Furthermore, a single package 10 has been described. It is contemplated, however, that each package 10 may include a plurality of interior compartments 11 that may be separately opened. Each compartment may contain a dispensing assembly 20 and a medicament container 30. Alternatively, one compartment may contain a dispensing assembly and a medicament container, while the remaining compartments contain additional doses of medication in medicament containers 30 that are loaded into the dispensing assembly by the patient or health care provider when opened. Thus, it is intended that the present invention covers the modifications and variations of the invention, provided they come within the scope of the appended claims and their equivalents.

What is claimed is:

1. A medicament dispensing kit for administering a predetermined dose of medication, the medicament dispensing kit comprising:
   a predetermined dose of medication;
   a medicament container containing the predetermined dose of medication, the container comprising a front end sealing assembly that seals the dose of medication in the container, the front end sealing assembly having a passageway operable to vent gases from the container during a container filling operation and operable to pass the predetermined dose of medication there through from the container during a medication dispensing operation, the front end sealing assembly having a first end and a second end, the passageway formed in an exterior surface of the front end sealing assembly and extending along the exterior surface from the first end partially toward the second end;
   a dispensing assembly configured to receive the medicament container therein, wherein the dispensing assembly dispenses the predetermined dose of medication upon activation by a user;
   a gas absorbing component; and
   a sealed package forming a sealed interior compartment flushed with an inert gas to remove oxygen, wherein the sealed interior compartment contains the medicament container having the predetermined dose of medication located therein, the dispensing assembly, the inert gas, and the gas absorbing component.

2. The dispensing kit according to claim 1, wherein the medicament container comprises:
   a cartridge assembly for receiving the predetermined dose of medication and the front end sealing assembly; and
   an internal sealing assembly positioned in the cartridge assembly.

3. The dispensing kit according to claim 2, wherein at least one sealing assembly is formed from one of an oxygen absorbing material, an oxygen barrier material, and an oxygen permeable material.

4. The dispensing kit according to claim 3, wherein the oxygen absorbing material and the oxygen barrier material are rubber.

5. The dispensing kit according to claim 2, wherein the predetermined dose of medication is sealed within the cartridge assembly by the front end and internal sealing assemblies in an environment containing an inert gas.

6. The dispensing kit according to claim 2, wherein the internal sealing assembly is operable to slide toward the front end sealing assembly during a dispensing operation.

7. The dispensing kit according to claim 1, wherein the dispensing assembly includes a housing having an interior compartment formed therein, wherein the housing is configured to be secured to a portion of the medicament container.

8. The dispensing kit according to claim 7, wherein the front end sealing assembly moves into the interior compartment of the housing upon activation of the dispensing assembly.

9. The dispensing kit according to claim 8, wherein the front end sealing assembly includes at least one projection extending from an end portion of the front end sealing assembly, the at least one projection configured to contact a surface of the interior compartment during a dispensing operation.

10. The dispensing kit according to claim 9, wherein the dispensing assembly further includes a needle for injecting the predetermined dose of medication into the user upon activation of the dispensing assembly, wherein the at least one projection is positioned adjacent an end portion of the needle during a dispensing operation.

11. The dispensing kit according to claim 1, wherein the sealed package includes a plurality of sealed interior compartments, wherein each sealed compartment contains a medicament container having the predetermined dose of medication located therein, a dispensing assembly, an oxygen absorbing material, and an inert gas located therein.

12. The dispensing kit according to claim 11, wherein the sealed package is a high barrier pouch.

13. The dispensing kit according to claim 12, wherein the high barrier pouch is a laminated pouch having more than one layer.

14. The dispensing kit according to claim 13, wherein one of the layers of the laminated pouch contains an aluminum foil layer.

15. The dispensing kit according to claim 13, wherein one of the layers contains the oxygen absorbing component.

16. The dispensing kit according to claim 1, wherein the sealed package is a high barrier pouch.

17. The dispensing kit according to claim 16, wherein the high barrier pouch is a laminated pouch having more than one layer.

18. The dispensing kit according to claim 17, wherein one of the layers of the laminated pouch contains an aluminum foil layer.

19. The dispensing kit according to claim 17, wherein one of the layers contains the oxygen absorbing component.

20. The dispensing kit according to claim 1, wherein the dispensing assembly comprises:
a dispensing element for administering the predetermined dose of medication from the medicament container in response to activation of the dispensing assembly.

21. The dispensing kit according to claim 20, wherein the dispensing element further includes a needle for injecting the predetermined dose of medication into the user upon activation of the dispensing assembly.

22. The dispensing kit according to claim 1, wherein the predetermined dose of medication includes one of dihydroergotamine, epinephrine and an oxygen sensitive medicament.

23. The dispensing kit according to claim 1, wherein a second passageway is formed in the exterior surface of the front end sealing assembly.

24. The dispensing kit according to claim 1, wherein the front end sealing assembly moves from a venting position to a sealing position after the filling operation and from the sealing position to a dispensing position in response to activation of the dispensing assembly, the venting position and the dispensing position being the same position with respect to the medicament container.

25. The dispensing kit according to claim 1, wherein the dispensing assembly contains the gas absorbing component.

26. The dispensing kit according to claim 1, wherein the medicament container contains the gas absorbing component.

27. The dispensing kit according to claim 1, wherein at least a portion of the dispensing assembly is formed from a gas absorbing material.

28. The dispensing kit according to claim 1, further comprising a rigid secondary package, wherein the sealed package is located within an interior of the rigid secondary package.

29. A medicament dispensing kit for administering a predetermined dose of medication, the medicament dispensing kit comprising:

a predetermined dose of medication;
a medicament container containing the predetermined dose of medication and comprising:
  a cartridge assembly operative to receive the predetermined dose of medication and having an opening formed therein, and
  a movable sealing assembly operative in a first position to seal the opening in the cartridge assembly, the sealing assembly comprising:
    an end portion having a plurality of projections extending therefrom, and
    a venting assembly operative to vent a gas from an interior of the cartridge assembly when the sealing assembly is in a second position after the predetermined dose of medication has been filled therein and before activation of a dispensing operation;
a dispensing assembly configured to receive the medicament container therein, wherein the dispensing assembly dispenses the predetermined dose of medication upon activation by a user, the activation causing the sealing assembly to move to the second position wherein the plurality of projections contacts an interior surface of the dispensing assembly to form a liquid communication path allowing the predetermined dose of medication to pass through the venting assembly, around the end portion, and through a space created between the projections and the interior surface of the dispensing assembly;
a gas absorbing component; and
a sealed package forming a sealed interior compartment, the sealed interior compartment including the medicament container having the predetermined dose of medication located therein and the dispensing assembly.

30. The dispensing kit according to claim 29 wherein the sealed package is a high barrier pouch.

31. The dispensing kit according to claim 30 wherein the high barrier pouch is a laminated pouch having more than one layer.

32. The dispensing kit according to claim 31 wherein one of the layers of the laminated pouch contains an aluminum foil layer.

33. The dispensing kit according to claim 31 wherein one of the layers contains the gas absorbing component.

34. The dispensing kit according to claim 29 wherein the sealing assembly is formed from one of an oxygen absorbing material, an oxygen barrier material, and an oxygen permeable material.

35. The dispensing kit according to claim 34 wherein the oxygen absorbing material and the oxygen barrier material are rubber.

36. The dispensing kit according to claim 29 further comprising an inert gas located within the sealed interior compartment.

37. The dispensing kit according to claim 29 wherein the predetermined dose of medication includes one of dihydroergotamine, epinephrine, and an oxygen sensitive medicament.

38. The dispensing kit according to claim 29 wherein the gas absorbing component comprises an oxygen absorbing substance.

39. The dispensing kit according to claim 29 wherein the dispensing assembly includes a needle for injecting the predetermined dose of medication into a user upon activation of the dispensing assembly.

40. The dispensing kit according to claim 29 wherein the dispensing assembly contains the gas absorbing component.

41. The dispensing kit according to claim 29 wherein the medicament container contains the gas absorbing component.

42. The dispensing kit according to claim 29 wherein at least a portion of the dispensing assembly is formed from a gas absorbing material.

43. The dispensing kit according to claim 29 further comprising a rigid secondary package, the sealed package located within an interior of the rigid secondary package.

44. The dispensing kit according to claim 29 wherein the sealed package forms a sealed interior compartment flushed with an inert gas to remove oxygen, the sealed interior compartment including the inert gas therein.

45. The dispensing kit according to claim 29 wherein the venting assembly comprises a body portion having a passageway formed in and extending along an exterior surface of the body portion.

46. A medicament dispensing kit for administering a predetermined dose of medication, the medicament dispensing kit comprising:
a predetermined dose of medication;
a medicament container containing the predetermined dose of medication, the container comprising a front end sealing assembly having a storage position relative to the container which seals the dose of medication in the container, the front end sealing assembly comprising a body portion that frictionally engages an inner surface of the container, the body portion having a passageway formed in a portion of an exterior surface of the body portion, the passageway operable to vent gases from the container during a container filling operation and operable to pass the predetermined dose of medication there through from the container during a medication dispensing operation;
a dispensing assembly configured to receive the medicament container therein and to dispense the predetermined dose of medication upon activation by a user; and
a sealed package forming a sealed interior compartment that has the dispensing assembly and the medicament container having the predetermined dose of medication located therein.

47. The dispensing kit according to claim 46, wherein the front end sealing assembly moves from a venting position to a sealing position after the filling operation and from the sealing position to a dispensing position in response to activation of the dispensing assembly.

48. The dispensing kit according to claim 47, wherein the venting position and the dispensing position are the same position with respect to the medicament container.

49. The dispensing kit according to claim 46 wherein the sealed package comprises a laminated pouch having more than one layer.

50. The dispensing kit according to claim 46 wherein one of the layers comprises an aluminum foil layer.

51. The dispensing kit according to claim 49 wherein one of the layers comprises a gas absorbing component.

52. The dispensing kit according to claim 46 further comprising a gas absorbing component.

53. The dispensing kit according to claim 46 wherein the dispensing assembly comprises a gas absorbing component.

54. The dispensing kit according to claim 46 wherein the medicament container comprises a gas absorbing component.

55. The dispensing kit according to claim 46 wherein the sealed package is flushed with an inert gas to remove oxygen from the interior compartment.

56. The dispensing kit according to claim 46, wherein the front end sealing assembly is formed from rubber.

57. The dispensing kit according to claim 46, wherein the predetermined dose of medication includes an oxygen sensitive medicament.

58. The dispensing kit according to claim 46, wherein the dispensing assembly includes a needle for injecting the predetermined dose of medication into the user upon activation of the dispensing assembly.

59. The dispensing kit according to claim 46, wherein the dispensing assembly includes a nasal sprayer for spraying the predetermined dose of medication into the user upon activation of the dispensing assembly.

60. The dispensing kit according to claim 46 wherein the sealed package comprises a high barrier pouch.

* * * * *